United States Patent [19]

Garcia

[11] Patent Number: 4,945,925
[45] Date of Patent: Aug. 7, 1990

[54] ARM/LEG BOARD

[76] Inventor: Rosa F. Garcia, 4054 W. 8th La., Hialeah, Fla. 33012

[21] Appl. No.: 354,888

[22] Filed: May 22, 1989

[51] Int. Cl.$^5$ .............................................. A61F 5/04
[52] U.S. Cl. ................................... 128/877; 128/878; 128/77
[58] Field of Search ................ 128/869, 870, 876–879, 128/882, 77, 83, 87 R

[56] References Cited

U.S. PATENT DOCUMENTS

| | | | |
|---|---|---|---|
| 2,266,230 | 12/1941 | Mazzeo et al. | 128/877 |
| 3,469,268 | 9/1969 | Phillips | 128/870 |
| 4,286,588 | 9/1981 | Lovegrove | 128/877 |
| 4,502,477 | 3/1985 | Lewis | 128/879 |
| 4,503,849 | 3/1985 | Morgan et al. | 128/877 |

Primary Examiner—Robert A. Hafer
Assistant Examiner—Kerry Owens

[57] ABSTRACT

A supporting board or like structure designed to be attached to the limbs including arms, legs, etc. of a patient to facilitate the securement of an I.V. catheter assembly to the patient and the immobilization of the catheter and the I.V. tubing to guard against inadvertent disengagement or removal of the catheter from the supported limb. A substantially rigid material base includes an absorbent material covering and a portion projecting outwardly from a transverse segment of the supporting base wherein the overall shape, structure and dimensioning of the board as well as the outwardly extending projection reduces problems relating to the prolonged immobilization of the limb.

1 Claim, 1 Drawing Sheet

U.S. Patent
Aug. 7, 1990
4,945,925
FIG. 1
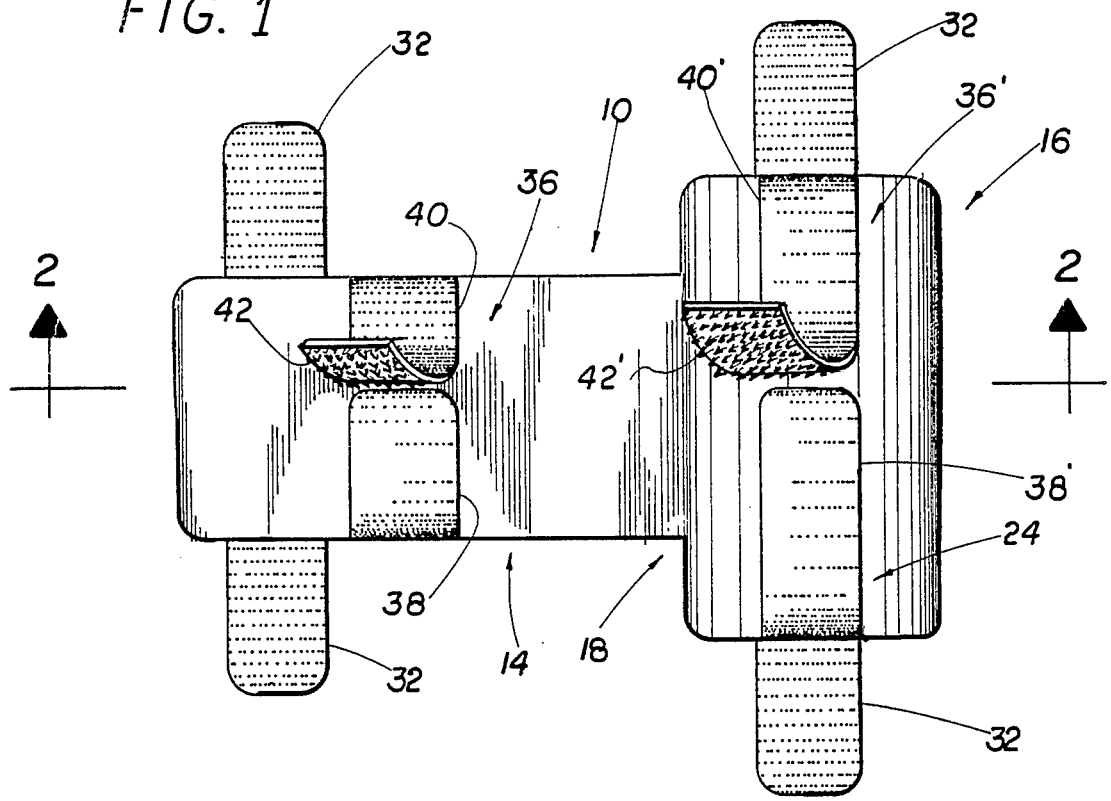
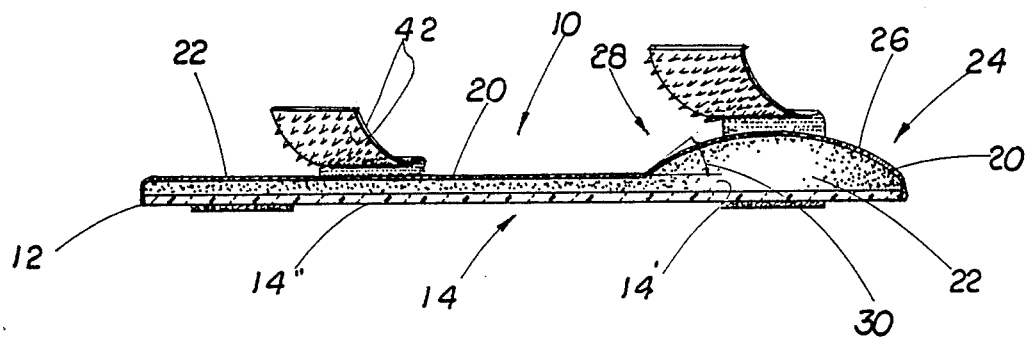
FIG. 2
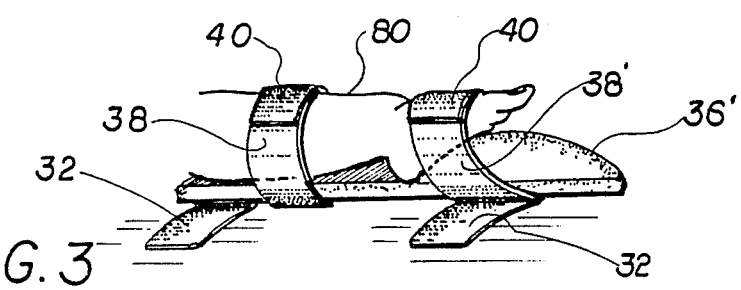
FIG. 3

ARM/LEG BOARD

BACKGROUND OF THE INVENTION

1. Field of the Invention

A support assembly in the form of an arm or leg board designed to facilitate the maintenance of an I.V. catheter within the vein of a patient while maintaining the appropriate limb in a secure, stable and comfortable position which will not cause harm to the patient.

2. Description of the Prior Art

Utilization of arm boards or leg boards to support and stabilize a patients limb when an I.V. set-up is attached to the limb is a common medical practice. However, particularly when dealing with premature or newborn infants, certain problems are also well recognized. Specifically, when an I.V. catheter is placed in the vein of the foot or lower leg, a supporting board is attached to the foot such that the foot is commonly forced into a downwardly extended position. This position is frequently maintained for a long period of time resulting in a shortening of the achilles tendon. Therefore, when the catheter is removed and the support board is detached from the infants leg, physical therapy is often required for purposes of lengthening or rehabilitating the achilles tendon.

Other common features associated with the use of boards of this type is the use of tape which frequently results in skin irritation to the patient particularly when the patient is an infant or child. In order to stabilize the I.V. set-up, the tape is applied to the I.V. frequently in covering relation to the site of entry of the catheter and also to the I.V. tubing. This will reduce the possibility of removal of the catheter from the patient during normal attempted movement of the limb.

Support boards of the type set-forth above are commercially available under the trademark Neo-guard Limboard, manufactured by Cas Medical Systems, Inc. This type of board is frequently used with infants including prematures, newborns as well as the pediatric age group.

Other advancements in the prior art are represented by the following Mazzeo et al. U.S. Pat. No. 2,266,230 discloses an arm rest for intravenous injection including a relatively complicated clamp and/or holding assembly and a brace and/or support structure for adjustable positioning of the clamp means. Similarly, Roberts U.S. Pat. No. 3,722,508 discloses an infusion guard and immobilizer useful in intravenous infusions and including a rigid member having one surface conforming to the portion of a limb spanning a joint such as for example an elbow, wrist or ankle. Velcro attaching straps are further mounted so as to grip or otherwise secure the assembly to the body portion.

Marais, U.S. Pat. No. 4,316,461 discloses an intravenous vascular stabilizer in which a base has a major medial longitudinal aperture or slot being adapted for positioning so that the edges of the slot embrace a vein. The slot is defined by an arched connector or hood portion to rigify the slot and to protect a needle type catheter in an inserted position.

Based on the above, numerous immobilization or support assemblies are well known in the art. While it is assumed that structures of this type are functional and operative for their intended purpose, it is apparent that many of these types of structures are perhaps overly complicated resulting in excessive initial cost and maintenance expense. Further, arm or leg boards of the type set forth above, do not overcome the harmful distending of the foot, or other portions of the body, resulting in the necessity for physical therapy to rehabilitate affected members of the body such as the achilles tendon.

There is an obvious need in the medical profession for a support assembly of the type set forth herein which overcomes the aforementioned disadvantages by properly, comfortably and safely positioning the limbs of the human body so as to not damage cooperative parts including the achilles tendon when the board is maintained in place to accomplish immobilization for prolonged periods. This is particularly important when dealing with premature infants, newborns and to perhaps a lesser extent patients of the adult population.

SUMMARY OF THE INVENTION

The present invention is directed towards a support assembly commonly known as an arm board or leg board and used to facilitate immobilization of a limb for purposes of stabilizing I.V. catheters and I.V. tubes associated therewith. Particularly, the support assembly of the present invention is dimensioned, configured and structured to prevent any damage being done to any portion of the patient's limb by forced distended positioning in an unnatural position. As set forth above, one problem generally associated with leg boards used for immobilization when a catheter or I.V. set-up is applied is the forced positioning of the foot in an awkward, distended position for prolonged periods. This in turn serves to force the achilles tendon to shorten particularly in premature or new born infants. The result is the necessity of physical therapy to rehabilitate the achilles tendon.

The structure and configuration of the support assembly of the present invention overcomes this problem by providing a base formed of at least semi-rigid material and having an elongated configuration of varying size depending upon the particular patient application for which it is intended. The base further includes a second portion arranged integrally or fixedly at one end of the first portion and oriented transversely thereto such that the opposite ends of the second transverse portion extends preferably an equal distance outwardly from opposite sides of the first portion.

A covering means in the form of a fluid absorbent cover is disposed in overlying, covering relation to exposed surfaces of the base. The material from which this covering means is formed is disposed in direct confronting relation with the skin of the patient and therefore should be formed of a non-irritating material.

An important feature of the present invention also includes an outwardly projecting portion extending along substantially the entire length of the second or transverse portion of the base in overlying covering relation to an outer exposed surface thereof. Preferably, this outer projection is formed of a soft, flexible, cushioning material in order to aid in the comfort to the patient when the support assembly is so applied. Further, the outer projection is specifically dimensioned and configured s that an attached and supported limb, such as a foot or the like, is comfortably positioned in the dorsiplex position which is the position of function.

More specifically, the angle of incidence of the outwardly projecting portion with the outer exposed portion of the first portion of the base is substantially thirty degrees which is recognized as the position of function of both upper and lower extremities. The result is a more comfortable positioning of the limb on the board and a reduction in strain or tension on the attendant muscles and tendons associated with the body portion attached to the subject support assembly.

The subject assembly further includes attachment means in the form of a plurality of spaced-apart wing members extending outwardly from peripheral portions of the base and being formed of a flexible, penetrable material. These wing members may be attached to the sheet, bedding or like supporting surface on which the support board of the present invention is normally positioned. Such attachment, for purposes of immobilization of the securement limb is accomplished by pins or the like.

It should be readily apparent therefore that the support assembly of the present invention facilitates the securement of the I.V. as well as the I.V. tubing to the board or to the patient without the excessive use of tape. Further securement of the I.V. can occur without obscuring the actual site of penetration which is common with support boards of this type currently in use.

The present invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a top plane view of the support assembly of the present invention.

FIG. 2 is a longitudinal sectional view along line 2—2 of FIG. 1.

FIG. 3 is a perspective view of an infants foot attached to the support assembly in the proper manner.

Like reference numerals refer to like parts throughout the several views of the drawings.

DETAILED DESCRIPTION OF THE PREFERRED EMBODIMENT

As shown in FIGS. 1 and 2, the present invention is directed towards a support assembly generally indicated as 10 which is specifically designed to hold a limb of a patient, particularly an infant, in a substantially stable position so that an I.V. set-up may also be stabilized while secured to the patient. The assembly 10 also includes a base portion 12 formed preferably of a rigid or at least semi-rigid material and having an elongated first portion generally indicated as 14. In addition, a second elongated portion 16 is secured integrally or fixedly at one end 18 of the first portion 14 and extends transversely relative to the longitudinal axis thereof. More specifically, in a preferred embodiment shown in FIGS. 1 and 2, the second elongated transverse portion 16 extends outwardly from longitudinal opposite sides of the first portion 14 in substantially equal distance as shown.

The first portion and the second portion includes a substantially absorbent material covering 20 extending over an exposed outer surface thereof. This covering is disposed in confronting relation with the limb of the patient.

A cushioning structure or material as at 22 is disposed immediately beneath the covering means 20 and extends along the length of the first portion 14 as well as the second, transverse portion 16 as clearly shown. The cushioning material 22 may be formed from any of a variety of materials and is structured to be both soft and resilient and generally to provide comfort to a portion of the arm, hand, leg, foot, etc. attached in confronting relation to the covering means.

An important feature of the present invention is the existence of an outwardly projecting portion generally indicated as 24 wherein the outwardly projecting portion 24 is defined at least in part by a greater transverse dimension or thickness of the cushioning means 22 extending outwardly from a corresponding surface portion of the base 14 as at 14'. Further, the outer surface configuration as at 26 of the outer projecting portion 24 has a preferably curvilinear configuration and, at an angle of incidence at the junction thereof generally indicated as 28 is formed at an angle of incidence of substantially 30 degrees. The angle, for purposes of clarity, is indicated as at 30. Such "angle of incidence" being 30 degrees is preferred based on a confronting position of a hand, foot, etc into a recognized "position of function". The result of course is a more comfortable positioning of the limb and a reduction in strain or tension of the attendant muscles and tendons associated with the body portion attached to the subject support assembly.

Other features associated with the present invention include attachment means in the form of at least one but preferably a plurality of wing members 32 extending outwardly from the periphery or applicable portions thereof of the base in covering or at least partially overlying, confronting relation to the bed sheets or other surface on which the under portion 14" of the base 14 is disposed when in its operative position attached to a patient. Accordingly, the wing members 32 should be substantially flexible to facilitate adequate positioning thereof and also in at least one embodiment should be penetrable by a pin or like sharp pointed connector. Other means or attaching the wing members 32 to a given supporting surface includes tape or any other applicable means.

It should further be noted that while the wing members 32 are shown in spaced apart relation to one another, their actual size and shape may also still be within the intended scope of the present invention.

The structure of the present invention further includes a mounting means for attachment of the assembly 10 to the designated limb of the patient's body. In a preferred embodiment, the mounting means includes at least one strap assembly generally indicated as 36 including two strap members 38 and 40 attached at opposite ends thereof to the base and/or cushioning means and extending outwardly therefrom. Each of the straps 38 and 40 includes a free end having appropriate connector facilities as at 42 attachable thereto in order to facilitate removable attachment of the free ends to one another as clearly shown in FIGS. 1 and 2. As also shown in FIGS. 1 and 2, the mounting means may include more than one straps assemblies as at 36' including similarly structured and connected straps 38' and 40' having similar removable connectors as at 42' attached to the free ends thereof. The placement and number of the strap assemblies 36, 36' may vary depending upon the size and specific application for which the subject board is intended as well as the size or age of the patient.

An important feature of the present invention is the prevention of any damage being done specifically to the achilles tendon of newborn or premature infants to the extent that the foot will not have to be maintained in a distended position for prolonged periods of time in order to stabalize an I.V. set-up as is now common practice utilizing support leg boards of conventional design which are well known in the prior art. As shown in FIG. 3 the foot of a newborn or premature infant is shown in at least partially resting or supported position on the outer projecting portion in a manner which will alleviate the above noted problems concerning the prevention of damage being done specifically to the achilles tendon. In the position shown in FIG. 3 the foot will not have to be maintained in a distended position since the support provided by the projecting portion 24 will alleviate the requirement for the aforementioned distended orientation of the foot.

Now that the invention has been described,

What is claimed is:

1. A support assembly for the extremities of a patient including the arm/hand portions and the leg/foot portions of the body to facilitate attachment and stability of an I.V. set-up to the supported extremities, said assembly comprising:
   a. a base formed of a rigid material and including a first elongated portion and a second elongated portion disposed transversely to said first portion at one end thereof,
   b. covering means for covering said base and secured in overlying relation to an exposed surface of both said first and second portions of said base,
   c. said covering means including a layer of fluid absorbent materials secured to both said first and second portions and disposed in confronting relation to a body portion mounted thereon,
   d. an outwardly projecting portion mounted on said base at one end of said first portion and extending along an entire length of said second portion transversely to said first portion, said projecting portion having a substantially curvilinear outer surface and configured to orient and support a body portion attached thereto substantially at a position of function,
   e. attachment means including a plurality of wing members formed of a material capable of being penetrated by a sharp pointed connected and secured to said base at spaced apart locations along the periphery of said base and extending outwardly therefrom for attachment to a supporting surface on which said base is disposed, and
   f. mounting mean including a strap assembly secured to said base being dimensioned and configured to at least partially surround a body portion supported on the base in gripping relation thereto.

* * * * *